(12) United States Patent
Kolter et al.

(10) Patent No.: US 9,254,329 B2
(45) Date of Patent: Feb. 9, 2016

(54) STABLE PROTECTIVE COATINGS FOR PHARMACEUTICAL DOSAGE FORMS

(75) Inventors: Karl Kolter, Limburgerhof (DE); Maximilian Angel, Schifferstadt (DE); Thomas Breiner, Laudenbach (DE)

(73) Assignee: BASF SE, Ludwigshafen (DE)

( * ) Notice: Subject to any disclaimer, the term of this patent is extended or adjusted under 35 U.S.C. 154(b) by 822 days.

(21) Appl. No.: 13/504,722

(22) PCT Filed: Oct. 21, 2010

(86) PCT No.: PCT/EP2010/065848
§ 371 (c)(1),
(2), (4) Date: Apr. 27, 2012

(87) PCT Pub. No.: WO2011/051155
PCT Pub. Date: May 5, 2011

(65) Prior Publication Data
US 2012/0214917 A1   Aug. 23, 2012

Related U.S. Application Data

(60) Provisional application No. 61/258,220, filed on Nov. 5, 2009.

(30) Foreign Application Priority Data

Oct. 28, 2009 (EP) ..................... 09174372

(51) Int. Cl.
| C08K 3/00 | (2006.01) |
|---|---|
| A61K 47/32 | (2006.01) |
| C08K 3/26 | (2006.01) |
| C08K 3/24 | (2006.01) |
| C08K 5/00 | (2006.01) |
| C08K 5/13 | (2006.01) |
| C08K 5/17 | (2006.01) |
| A61K 9/10 | (2006.01) |
| A61K 9/28 | (2006.01) |
| C08F 220/14 | (2006.01) |
| C08F 220/34 | (2006.01) |

(52) U.S. Cl.
CPC . *A61K 47/32* (2013.01); *A61K 9/10* (2013.01); *A61K 9/2846* (2013.01); *C08F 220/14* (2013.01); *C08K 3/0041* (2013.01); *C08K 3/24* (2013.01); *C08K 3/26* (2013.01); *C08K 5/005* (2013.01); *C08K 5/13* (2013.01); *C08K 5/17* (2013.01); *C08K 5/175* (2013.01); *C08F 220/34* (2013.01); *C08K 2003/262* (2013.01)

(58) Field of Classification Search
CPC ... A61K 9/2846; A61K 47/32; C08K 3/0041; C08K 3/26; C08K 3/24; C08K 2003/262; C08K 5/005; C08K 5/13; C08K 5/17; C08K 5/175

See application file for complete search history.

(56) References Cited

U.S. PATENT DOCUMENTS

| 4,378,445 A | 3/1983 | Brasen et al. |
|---|---|---|
| 4,433,076 A | 2/1984 | Bauer et al. |
| 4,452,862 A | 6/1984 | Markert et al. |
| 6,624,210 B1 | 9/2003 | Petereit et al. |
| 6,696,085 B2 | 2/2004 | Rault et al. |
| 2003/0064036 A1 | 4/2003 | Petereit et al. |
| 2003/0068392 A1* | 4/2003 | Sackler ..................... 424/760 |
| 2004/0249035 A1 | 12/2004 | Petereit et al. |
| 2008/0299194 A1 | 12/2008 | Kolter et al. |
| 2011/0033532 A1 | 2/2011 | Angel et al. |
| 2011/0118510 A1 | 5/2011 | Weis et al. |
| 2012/0209030 A1 | 8/2012 | Lanver et al. |
| 2012/0209031 A1 | 8/2012 | Lanver et al. |

FOREIGN PATENT DOCUMENTS

| CA | 1009144 | 4/1977 |
|---|---|---|
| DE | 1090381 | 10/1960 |
| DE | 1219175 | 6/1966 |
| DE | 2135073 | 2/1973 |
| DE | 2512238 | 5/1976 |
| DE | 2838278 | 3/1979 |
| DE | 3049179 | 7/1982 |
| DE | 3426587 | 1/1986 |
| EP | 0058765 | 9/1982 |
| GB | 2006009 | 5/1979 |
| WO | WO-00/05307 | 2/2000 |
| WO | WO-02/067906 | 9/2002 |
| WO | WO-2004/019918 | 3/2004 |
| WO | WO-2005/055986 | 6/2005 |
| WO | WO-2005/056619 | 6/2005 |
| WO | WO-2007/071581 | 6/2007 |
| WO | WO-2009/016258 | 2/2009 |
| WO | WO-2010/012675 | 2/2010 |
| WO | WO-2011/048012 | 4/2011 |
| WO | WO-2011/048068 | 4/2011 |

OTHER PUBLICATIONS

"International Search Report and Written Opinion in PCT/EP2010/065848", mailed on Oct. 18, 2011, 7 pages.
"Machine Translation of DE1090381", 2 pages.

* cited by examiner

*Primary Examiner* — Peter D Mulcahy
(74) *Attorney, Agent, or Firm* — Servilla Whitney LLC

(57) ABSTRACT

A coating material, containing a mixture of i) a polymer obtained by radical polymerization from a) N,N-diethylaminoethyl methacrylate, and b) at least one radically polymerizable compound, selected from esters of α,β-ethylenically unsaturated mono- and dicarboxylic acids with $C_1$-$C_{18}$ alkanols, as component A, ii) one or more antioxidants as component B, iii) one or more plasticizers as component C, and iv) other excipients as components D, wherein the total amount of the mixture of components A-D is 100 wt. %.

18 Claims, No Drawings

STABLE PROTECTIVE COATINGS FOR PHARMACEUTICAL DOSAGE FORMS

CROSS-REFERENCE TO RELATED APPLICATIONS

This application is the National Stage entry of PCT/EP2010/065848, filed on Oct. 21, 2010, which claims priority to European Patent application number 09174372.4 filed on Oct. 28, 2009 and U.S. Provisional application No. 61/258,220 filed Nov. 5, 2009, the disclosures of which are incorporated herein by reference in their entireties.

FIELD

The present invention relates to coating materials for stable protective coatings for pharmaceutical dosage forms, which are provided with a film coating based on a cationic polymer, obtained by radical emulsion polymerization of a monomer mixture containing N,N-diethylaminoethyl methacrylate, for the purpose of masking taste or for protection against moisture.

BACKGROUND

DE-AS 1090381 describes a method of coating dosage forms with coating materials that are soluble in the stomach. These contain a copolymer of 20-80% of at least one amino ester of (meth)acrylic acid and 80-20% of a monomer that forms a water-insoluble polymerizate as homopolymer. The esters of acrylic acid and (meth)acrylic acid with N,N-dimethylaminoethanol, N,N-diethylaminoethanol, N,N-dimethylaminopropanol and N-(hydroxyethyl)morpholine are mentioned as concrete examples of suitable polymerizable amino esters. Lower esters of acrylic acid and preferably of (meth)acrylic acid, such as ethyl acrylate, methyl, butyl and hexyl (meth)acrylate are mentioned as suitable comonomers. They are produced by solution polymerization in an organic solvent; no example is given.

DE-AS 1219175 describes a method of production of preparations of active compounds for use in veterinary medicine, which are protected against the action of ruminal fluid of ruminants. For this purpose, these preparations are coated with copolymers containing N,N-dialkylaminoalkyl(meth)acrylamides and a comonomer, incorporated by polymerization, which is selected from (meth)acrylates, acrylonitrile and vinylic aromatics. Copolymers based on N,N-dialkylaminoalkyl(meth)acrylates are, according to the teaching of this document, regarded as disadvantageous, as the ester group, compared with the amide group, is saponified earlier in the basic environment.

DE-OS 2135073 describes coating materials for dosage forms that contain an aqueous polymer dispersion, with the polymer consisting to 10-55 wt. % of monomers with a carboxyl group and/or a monoalkyl- or dialkylaminoalkyl ester group. Diethylaminoethyl methacrylate (DEAEMA) is mentioned as a suitable monomer, in addition to many others. The lower esters of (meth)acrylic acid, preferably methyl methacrylate, (meth)acrylonitrile, vinylic aromatics, vinyl chloride and vinyl acetate, are mentioned as suitable comonomers. Production takes place by aqueous emulsion polymerization, preferably according to the fed-batch emulsion process. Actual emulsion polymerizates based on DEAEMA are not disclosed.

DE-AS 2512238 teaches, for the preparation of binders for pharmaceutical coatings with low residual monomer content, the use of a powder obtained by spray-drying of a polymer dispersion for the production of coating solutions for these dosage forms. Regarding the dispersions used for spray-drying, reference is made to DE 1090381, DE 1219175 and DE 2135073.

DE-OS 2838278 describes coatings for oral dosage forms for ruminants from a) at least one film-forming polymer with at least one basic amino group and with a nitrogen content of 3-14%, which is soluble within 24 hours in aqueous ruminal medium at a pH of more than 5.5, and b) at least one hydrophobic substance dispersed in the polymer, selected from $C_{12}$-$C_{32}$ fatty acids, aluminum salts of these fatty acids and/or polycarboxylic acids.

A solution in an organic solvent is used for production of the coating. A large number of nitrogen-containing homo- and copolymers are listed as suitable polymers, without going into suitable methods for their production. A copolymer of 40% N,N-diethylaminoethyl methacrylate is given as example 29, though without stating a method of production thereof.

GB 1324087 describes coating polymers for oral dosage forms for ruminants, which contain a) at least one N,N-dialkylaminoalkyl(meth)acrylate and b) at least one ethylenically unsaturated compound, which is selected from vinylic aromatics and derivatives thereof, vinyl esters, esters of (meth)acrylic acid and acrylonitrile, incorporated by polymerization. N,N-dimethylaminoethyl methacrylate (DMAEMA) and tert-butylaminoethyl methacrylate (TBAEMA) are disclosed as suitable monomers a). In particular, methyl methacrylate is regarded as unsuitable as comonomer b), as it tends to form fragile coatings. Bulk, suspension, solution and emulsion polymerization are stated as suitable methods of polymerization. The copolymers in the examples were produced by solution polymerization.

DE 3426587 A1 describes a method of coating dosage forms by applying a film of a liquid, film-forming coating material, which contains a dissolved polymerizate with tertiary ammonium salt side groups. For production of these polymer solutions, among other means, copolymers based on N,N-dialkylaminoalkyl(meth)acrylates can be transformed with aqueous inorganic or organic acids to aqueous solutions of ammonium salts.

DE 3049179 A1 is an additional application to DE 2512238 and relates to the use of a powder, obtained by spray-drying according to the teaching of the latter document, in the form of an aqueous suspension, which additionally contains a plasticizer, for the production of coatings by thermal gelation.

EP 0058765 A2 describes coating materials for dosage forms soluble or swellable in gastric juice, and contain, as binder, an emulsion polymerizate based on N,N-dialkylaminoalkyl(meth)acrylates, with a branched alkylene or aralkylene group, with at least three carbon atoms arranged in a straight chain, being located between the amino group and the (meth)acrylate group.

WO 2005/055986 and WO 2005/056619 describe polymers with pH-dependent swelling/dissolution behavior and use thereof in dosage forms.

WO 00/05307 relates to the preparation of coating materials and binders for dosage forms, which contain (meth)acrylate copolymers, having monomer residues with tertiary amino groups, and simple dry or aqueous further processing is said to be possible. For this, this document teaches a method in which (a) a copolymer of $C_1$-$C_4$ esters of (meth)acrylic acid and (meth)acrylate monomers, which have tertiary ammonium groups, (b) a plasticizer and (c) an emulsifier with an HLB value of at least 14, are mixed together and the coating material or binder is produced therefrom by melting, pouring, spreading or spraying, copolymer (a) being applied in the form of powder with an average particle size of 1-40 µm. The resultant processability is attributed to the provision of copolymer (a) in powder form with extremely small grain size.

WO 02/067906 relates to coatings and binders with improved permeability to water vapor relative to those described in WO 00/05307. The coatings and binders are produced with a mixture containing (a) a copolymer of $C_1$-$C_4$ esters of (meth)acrylic acid and other (meth)acrylate monomers with functional tertiary ammonium groups in powder form with an average particle size of 1-40 µm, (b) an emulsifier with an HLB value of at least 14 and (c) a $C_{12}$-$C_{18}$ monocarboxylic acid or a $C_{12}$-$C_{18}$ hydroxyl compound.

WO 2004/019918 describes coatings and binders that correspond, with respect to their composition, to those described in WO 00/05307 and WO 02/067906.

According to U.S. Pat. No. 6,696,085 B2, a methacrylic acid copolymer of type C is used as a disintegrant. The methacrylic acid copolymer of type C is an enteric polymer, which is insoluble at acid pH, but is water-soluble at pH of about 7, as in the oral cavity. In addition to a low breaking strength (<20N), the tablets have high friability (>7%) and have a high proportion of a coarse-grained disintegrant, in the region of 15 wt. %. Consequently they have low mechanical strength and produce an unpleasant, sandy sensation in the mouth, owing to the high proportion of coarse-grained disintegrant.

The matrix components based on sugar alcohols, disintegrants and insoluble polymers are generally known for pharmaceutical applications from WO 2007/071581.

The production of the aqueous polymer dispersions of cationic polymers based on N,N-diethylaminoethyl methacrylate, as used according to the invention and their use for the coating of pharmaceuticals, is known from WO 2009/016258. However, the coating materials described in this document still leave something to be desired in stress storage with respect to stability of release and resistance to discoloration.

SUMMARY

One aspect of the present invention relates to coating materials containing a mixture of:
i) a polymer obtained by radical polymerization from
a) N,N-diethylaminoethyl methacrylate, and
b) at least one radically polymerizable compound, selected from esters of α,β-ethylenically unsaturated mono- and dicarboxylic acids with $C_1$-$C_8$ alkanols,
as component A,
ii) one or more antioxidants as component B,
iii) one or more plasticizers as component C, and
iv) other excipients as components D,
wherein the total amount of the mixture of components A-D is 100 wt. %.

Another aspect of the present invention relates to methods of using such coating materials as film coatings for pharmaceutical dosage forms, particularly as film coating that disintegrate quickly in an acid environment.

DETAILED DESCRIPTION

Embodiments of the present invention provide improved film coating materials for pharmaceutical dosage forms, which do not display any change in release behavior even in long-term or temperature-stressing storage. In some embodiments, the film coatings do not have an undesirable tendency to discolor.

Accordingly, coating materials were found in the form of aqueous polymer dispersions, containing
i) as component A, a polymer obtained by radical polymerization from
a) N,N-diethylaminoethyl methacrylate, and
b) at least one radically polymerizable compound, selected from esters of α,β-ethylenically unsaturated mono- and dicarboxylic acids with $C_1$-$C_8$ alkanols,
ii) one or more antioxidants as component B, and
iii) one or more plasticizers as component C,
iv) other excipients as components D.

The coating materials can contain, relative to the total weight of the dispersion
i) 1-45 wt. % of component A,
ii) 0.01-15 wt. % of component B,
iii) 0.1-15 wt. % of component C,
iv) 0-35 wt. % of components D.

Preferred coating materials contain
i) 1.5-42.5 wt. % of component A,
ii) 0.02-10 wt. % of component B,
iii) 0.15-12.5 wt. % of component C,
iv) 0-30 wt. % of components D.

Especially preferred coating materials contain, relative to the total weight of the dispersion
i) 4-40 wt. % of component A,
ii) 0.05-6 wt. % of component B,
iii) 0.4-8 wt. % of component C,
iv) 0.1-20 wt. % of components D.

The coating materials used are based on aqueous polymer dispersions, which are obtained by radical emulsion polymerization of a monomer mixture M), containing
a) N,N-diethylaminoethyl methacrylate, and
b) at least one radically polymerizable compound, selected from esters of α,β-ethylenically unsaturated mono- and dicarboxylic acids with $C_1$-$C_8$ alkanols,
in an aqueous medium at a pH of at least 8.

The coating materials in the form of aqueous polymer dispersions preferably do not obtain any additional organic solvents.

According to the invention, the coating materials are used for the production of pharmaceutical dosage forms that are to be released instantly in the acidic environment of the stomach. That is, the coatings according to the invention are soluble in gastric juice. "Released instantly" means, in this context, that after 60 min at least 80% of the active compound has been released. Coatings obtained according to the invention should not dissolve in the oral cavity and throat, in the neutral or almost neutral environment of the saliva.

The coating materials according to the invention can be used for masking taste or for protection from moisture. The coatings have very low permeability to water vapor, so that moisture-sensitive active compounds are protected.

Component A
Monomer a)
N,N-Diethylaminoethyl methacrylate is used according to the invention as monomer a).

For production of the aqueous polymer dispersions Pd) according to the invention, component a) is preferably used in an amount of 25-65 wt. %, especially preferably 30-60 wt. %, in particular 38-48 wt. %, and especially 43-47 wt. %, relative to the total weight of the monomers used for polymerization.

Monomer b)
Component b) is selected from esters of alpha, beta-ethylenically unsaturated mono- and dicarboxylic acids with $C_1$-$C_8$ alkanols.

Suitable compounds b) are methyl(meth)acrylate, methyl ethacrylate, ethyl(meth)acrylate, ethyl ethacrylate, n-propyl (meth)acrylate, isopropyl(meth)acrylate, n-butyl(meth)acrylate, sec-butyl(meth)acrylate, tert-butyl(meth)acrylate, tert-butyl ethacrylate, n-hexyl(meth)acrylate, n-heptyl(meth)acrylate, n-octyl(meth)acrylate, 1,1,3,3-tetramethylbutyl (meth)acrylate and ethylhexyl(meth)acrylate.

Especially preferably methyl methacrylate or a monomer mixture containing methyl methacrylate is used as component b).

For production of the aqueous polymer dispersions according to the invention, component b) is preferably used in an amount of 35-75 wt. %, especially preferably 40-70 wt. %, in particular 52-62 wt. %, and especially 53-57 wt. %, relative to the total weight of the monomers used for polymerization.

The monomer mixtures M) used for production of the polymer dispersions can additionally contain at least one other monomer c). The additional monomers c) are preferably selected from esters of alpha, beta-ethylenically unsaturated mono- and dicarboxylic acids with $C_9$-$C_{30}$ alkanols and $C_2$-$C_{30}$ alkane diols, amides of alpha, beta-ethylenically unsaturated mono- and dicarboxylic acids with $C_2$-$C_{30}$ amino alcohols, which have a primary or secondary amino group, primary amides of alpha, beta-ethylenically unsaturated monocarboxylic acids and N-alkyl and N,N-dialkyl derivatives thereof, N-vinyllactams, open-chain N-vinylamide compounds, esters of vinyl alcohol and allyl alcohol with $C_1$-$C_{30}$ monocarboxylic acids, vinyl ethers, vinylic aromatics, vinyl halides, vinylidene halides, $C_2$-$C_8$ monoolefins, unsaturated nitriles, nonaromatic hydrocarbons with at least two conjugated double bonds and mixtures thereof.

Suitable additional monomers c) are esters of alpha, beta-ethylenically unsaturated mono- and dicarboxylic acids with $C_9$-$C_{30}$ alkanols, such as n-nonyl(meth)acrylate, n-decyl(meth)acrylate, n-undecyl(meth)acrylate, tridecyl(meth)acrylate, myristyl(meth)acrylate, pentadecyl(meth)acrylate, palmityl(meth)acrylate, heptadecyl(meth)acrylate, nonadecyl(meth)acrylate, arachinyl(meth)acrylate, behenyl(meth)acrylate, lignoceryl(meth)acrylate, cerotinyl(meth)acrylate, melissinyl(meth)acrylate, palmitoleinyl(meth)acrylate, oleyl(meth)acrylate, linolyl(meth)acrylate, linolenyl(meth)acrylate, stearyl(meth)acrylate, lauryl(meth)acrylate and mixtures thereof.

Suitable additional monomers c) are moreover esters of alpha, beta-ethylenically unsaturated mono- and dicarboxylic acids with $C_2$-$C_{30}$ alkane diols, such as 2-hydroxyethylacrylate, 2-hydroxyethyl methacrylate, 2-hydroxyethyl ethacrylate, 2-hydroxypropylacrylate, 2-hydroxypropylmethacrylate, 3-hydroxypropylacrylate, 3-hydroxypropylmethacrylate, 3-hydroxybutylacrylate, 3-hydroxybutylmethacrylate, 4-hydroxybutylacrylate, 4-hydroxybutylmethacrylate, 6-hydroxyhexylacrylate, 6-hydroxyhexylmethacrylate, 3-hydroxy-2-ethylhexylacrylate, 3-hydroxy-2-ethylhexylmethacrylate etc.

Suitable additional monomers c) are moreover primary amides of alpha, beta-ethylenically unsaturated monocarboxylic acids and N-alkyl and N,N-dialkyl derivatives thereof, such as acrylic acid amide, methacrylic acid amide, N-methyl(meth)acrylamide, N-ethyl(meth)acrylamide, N-propyl(meth)acrylamide, N-(n-butyl)(meth)acrylamide, N-(tert-butyl)(meth)acrylamide, N-(n-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth)acrylamide, N-nonadecyl(meth)acrylamide, N-arachinyl(meth)acrylamide, N-behenyl(meth)acrylamide, N-lignoceryl(meth)acrylamide, N-cerotinyl(meth)acrylamide, N-melissinyl(meth)acrylamide, N-palmitoleinyl(meth)acrylamide, N-oleyl(meth)acrylamide, N-linolyl(meth)acrylamide, N-linolenyl(meth)acrylamide, N-stearyl(meth)acrylamide, N-lauryl(meth)acrylamide, N,N-dimethyl(meth)acrylamide, N,N-diethyl(meth)acrylamide, morpholinyl(meth)acrylamide.

Other suitable additional monomers c) are N-vinyllactams and derivatives thereof, which can have e.g. one or more $C_1$-$C_6$ alkyl substituents, such as methyl, ethyl, n-propyl, isopropyl, n-butyl, sec-butyl, tert-butyl etc. These include e.g. N-vinyl pyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. Preferably N-vinyl pyrrolidone and N-vinylcaprolactam are used.

Open-chain N-vinylamide compounds suitable as monomers c) are for example N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide. Suitable additional monomers c) are moreover vinyl acetate, vinyl propionate, vinyl butyrate and mixtures thereof.

Suitable additional monomers c) are moreover ethylene, propylene, isobutylene, butadiene, styrene, -methylstyrene, acrylonitrile, methacrylonitrile, vinyl chloride, vinylidene chloride, vinyl fluoride, vinylidene fluoride and mixtures thereof.

The aforementioned additional monomers c) can be used individually or in the form of any mixtures.

For production of the aqueous polymer dispersions) according to the invention, component c) is preferably used in an amount of 0-80 wt. %, relative to the total weight of the monomers used for polymerization. A special embodiment relates to polymer dispersions Pd), which do not contain any additional monomer c) incorporated by polymerization. If present, component c) is preferably used in an amount of 0.1-70 wt. %, especially preferably 1-60 wt. %, in particular 5-50 wt. %, relative to the total weight of the monomers used for polymerization.

Preferably no monomer c) is used.

Monomer d)

The monomer mixtures M) used for production of the polymer dispersions can contain, additionally to compound a), at least one other compound d) different from the latter with a radically polymerizable alpha, beta-ethylenically unsaturated double bond and at least one cationogenic and/or cationic group per molecule, incorporated by polymerization.

Preferably the cationogenic or cationic groups of component d) are nitrogen-containing groups, such as primary, secondary and tertiary amino groups and quaternary ammonium groups. Preferably the nitrogen-containing groups are tertiary amino groups or quaternary ammonium groups. Charged cationic groups can be produced from the amine nitrogens either by protonation, e.g. with monovalent or polyvalent carboxylic acids, such as lactic acid or tartaric acid, or mineral acids, such as phosphoric acid, sulfuric acid and hydrochloric acid, or by quaternization, e.g. with alkylating agents, such as $C_1$-$C_4$ alkyl halides or sulfates. Examples of said alkylating agents are ethyl chloride, ethyl bromide, methyl chloride, methyl bromide, dimethyl sulfate and diethyl sulfate. Suitable compounds d) are e.g. the esters of alpha, beta-ethylenically unsaturated mono- and dicarboxylic acids with amino alcohols that are different from DEAEMA. Preferred amino alcohols are $C_2$-$C_{12}$ amino alcohols, which are $C_1$-$C_8$-mono- or dialkylated on the amine nitrogen. For example acrylic acid, methacrylic acid, fumaric acid, maleic acid, itaconic acid, crotonic acid, maleic anhydride, monobutylmaleate and mixtures thereof are suitable as the acid component of these esters. Preferably acrylic acid, methacrylic acid and mixtures thereof are used as the acid component of these esters.

Suitable additional compounds d) are N,N-dimethylaminomethyl(meth)acrylate, N,N-dimethylaminoethyl(meth)acrylate, N,N-diethylaminoethylacrylate, N,N-dimethylaminopropyl(meth)acrylate, N,N-diethylaminopropyl(meth)acrylate and N,N-dimethylaminocyclohexyl(meth)acrylate.

Suitable monomers d) are furthermore the amides of the aforementioned alpha, beta-ethylenically unsaturated mono- and dicarboxylic acids with diamines, which have at least one primary or secondary amino group. Diamines that have a tertiary and a primary or secondary amino group are preferred.

These include N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)-butyl]methacrylamide, N-[2-(diethylamino)ethyl]acrylamide, N-[4-(dimethylamino)cyclohexyl]acrylamide, N-[4-(dimethylamino)cyclohexyl]methacrylamide etc.

Suitable monomers d) are furthermore N,N-diallyl amines and N,N-diallyl-N-alkyl amines and their salts of acid addition and quaternization products. Alkyl then preferably stands for $C_1$-$C_{24}$ alkyl. N,N-diallyl-N-methyl amine and N,N-diallyl-N,N-dimethylammonium compounds, e.g. the chlorides and bromides, are preferred.

Suitable monomers d) are furthermore vinyl- and allyl-substituted nitrogen heterocycles, such as N-vinylimidazole, N-vinyl-2-methylimidazole, vinyl- and allyl-substituted heteroaromatic compounds, such as 2- and 4-vinylpyridine, 2- and 4-allylpyridine, and salts thereof.

For production of the aqueous polymer dispersions Pd) according to the invention, the monomer d), if present, is preferably used in an amount such that the sum of the amounts of monomers a) and of monomers d) is in the range 25-65 wt. %, especially preferably 30-60 wt. %, relative to the total weight of the monomers used for polymerization.

For production of the aqueous polymer dispersions Pd) according to the invention, component d) is preferably used in an amount of 0-50 wt. %, relative to the total weight of the monomers used for polymerization.

As already stated, it was found, surprisingly, that the polymer dispersions Pd) according to the invention and used according to the invention, based on DEAEMA (component a)), have a particularly good profile of properties. This profile of properties can as a rule be achieved without using additional monomers with cationogenic/cationic groups. A special embodiment therefore relates to polymer dispersions Pd) that do not contain any additional monomer d) incorporated by polymerization.

If present, component d) is preferably used in an amount of 0.1-40 wt. %, especially preferably 1-30 wt. %, in particular 2-25 wt. %, relative to the total weight of the monomers used for polymerization.

In an especially preferred embodiment of the method according to the invention, a monomer mixture M) is used that consists of
43-47 wt. %, relative to the total weight of the monomers used for polymerization, of N,N-diethylaminoethyl methacrylate a), and
53-57 wt. %, relative to the total weight of the monomers used for polymerization, of at least one compound b), in particular methyl methacrylate.

For production of the polymerizates by radical emulsion polymerization, reference is hereby expressly made to the disclosure of WO 2009/016258, in which the production and preferred embodiments are described in detail.

The polymers contained in the dispersions according to the invention preferably have an average molecular weight $M_w$, determined by gel permeation chromatography, in the range 30000-500000, especially preferably 60000-140000, in particular 80000-120000 g/mol.

The polymers contained in the dispersions Pd) according to the invention preferably have a K value (determined according to Fikentscher on a 1% solution in N-methylpyrrolidone (NMP)) in the range 40-60.

The glass transition temperature $T_g$ (determined by DSC) is preferably in the range 4070° C., especially preferably 52-62° C.

The polymers contained in the dispersions according to the invention are essentially random copolymers.

The average particle diameter of the polymer particles contained in the polymer dispersion (determined by means of an analytical ultracentrifuge) is preferably in the range from 70 to 200 nm, especially preferably from 80 to 150 nm, in particular from 90 to 120 nm. The particle size distribution is preferably substantially unimodal.

The LT value of the dispersions according to the invention, determined on a 0.01% dispersion in water (2.5 cm cuvette, white light) is preferably at least 70%, especially preferably at least 80%. Determination of the light transmission is described e.g. in Dieter Distler, Aqueous Polymer Dispersions, Wiley-VCH (1999), p. 40.

The solids content of the dispersions according to the invention is preferably 10-50 wt. %, especially preferably 20-40 wt. %. In the case of purification of the dispersion by ultrafiltration the dispersions according to the invention preferably have solid contents that are within this range before and after ultrafiltration. It is, of course, also possible for a diluted polymer dispersion to be submitted to concentration by ultrafiltration.

The dispersions used according to the invention for masking taste have, for example even at a solids content of 30 wt. %, extremely low viscosities preferably of less than 50 mPas, especially preferably less than 25 mPas and in particular less than 10 mPas (values determined with a Brookfield viscosimeter at 20° C. and 100 $s^{-1}$). Such low viscosities are particularly important for many applications.

The charge of the polymers contained in the dispersions according to the invention depends on the pH of the dispersion. The isoelectric point is preferably in a pH range from about 7.5 to 8.5. The prepared dispersion preferably has a pH in the range 8-10, especially preferably 8.5-9.5 (at a solids content of 30 wt. %). It is advantageous for the pH of the prepared dispersion to be selected higher (more alkaline) than its isoelectric point, unless dissolution or swelling of the polymer particles contained in the dispersion is desired. Therefore the dispersions according to the invention are preferably basic dispersions.

The polymer dispersions according to the invention are characterized by their pH-dependent solubility. The pH range in which the dispersion dissolves on acidification can be adjusted e.g. by the amount of N,N-diethylaminoethyl methacrylate (monomer a) incorporated by polymerization, and optionally the use of additional monomers with cationogenic/cationic groups (monomer d). Preferably the polymers contained in the polymer dispersions Pd) according to the invention dissolve at a pH of max. 6.8, especially preferably at a pH of max. 6.0.

According to a preferred embodiment, polymer dispersions are used that contain a polymer that contains 43-47 wt. %, relative to the total weight of the monomers used for polymerization, of N,N-diethylaminoethyl methacrylate a), and 53-57 wt. %, relative to the total weight of the monomers used for polymerization, of at least one compound b)

as the only monomers, incorporated by polymerization.

Component B

The coating materials according to the invention contain, in addition to the polymer, one or more antioxidants or a combination of antioxidants.

Basically, mainly the following agents, the combinations listed or other combinations are suitable as antioxidants for improving the release stability:

N-acetylcysteine, allantoin, arginine, arginine+butyl hydroxytoluene, arginine+N-acetylcysteine, ascorbyl palmitate, aspartic acid, biotin, butyl hydroxyanisole, butyl hydroxytoluene, butyl hydroxytoluene+calcium carbonate, butyl hydroxytoluene+Na-EDTA, butyl hydroxytoluene+N-acetylcysteine calcium-bis[monoethyl(3,5-di-tert-butyl-4-hydroxy-benzyl)phosphonate], catechol, citric acid, cysteamine, ethylhexylthioglycolate, gallic acid, hypophosphorous acid, caffeic acid, potassium iodide, creatine, creatinine, copper(I) chloride, copper(II) chloride, lysine, MEHQ, methionine, Na-EDTA, sodium carbonate, sodium dihydrogen phosphate, disodium hydrogen phosphate, sodium propionate, nordihydroguaiaretic acid, orotic acid, penicillamine, phosphoric acid, propyl gallate, resveratrol, riboflavin, spermidine, thioglycolic acid, tocopherol, tocopherol acetate, trometamol, tyrosine, tartaric acid.

Basically, mainly the following agents, the combinations listed or other combinations are suitable for improving resistance to yellowing:

oleic acid, simethicone, butyl hydroxytoluene, sodium hydrogen sulfite, tocopherol, sodium dihydrogen citrate, sodium hypochlorite, sodium hypophosphite, disodium hydrogen phosphate, tocopherol, tocopherol acetate, arginine, butyl hydroxytoluene+Na-EDTA, acetylcysteine (N-acetylcysteine), butyl hydroxytoluene, allantoin, butyl hydroxyanisole, sodium carbonate, cysteamine, N-acetylcysteine.

Preferred antioxidants are compounds of the phenol type. Preferred phenolic compounds are for example butyl hydroxytoluene or butyl hydroxyanisole, as they completely prevent both delay in dissolution and yellowing. Other suitable products are: catechol, gallic acid or esters thereof, tocopherol, caffeic acid, hydroquinone monomethyl ether (MEHQ), nordihydroguaiaretic acid, resveratrol.

Other preferred antioxidants are thiolic compounds, such as N-acetylcysteine, cysteamine, thioglycolic acid.

Basic amino acids such as arginine and lysine are also preferred.

Preferred antioxidants are also alkali metal carbonates or alkali metal bicarbonates, in particular the sodium salts, preferably sodium carbonate.

Combinations with EDTA, in particular Na-EDTA or with citric acid, are also preferred.

N-Acetylcysteine, arginine, lysine, butyl hydroxytoluene, butyl hydroxytoluene+Na EDTA, and sodium carbonate or combinations thereof, are especially preferred.

All the stated compounds or classes of compounds can also be used in combination.

The antioxidants are used in amounts of 0.1-30, preferably 0.3-20, especially preferably 0.5-12 wt. %, relative to the total amount of solid matter in the coating material.

Component C

Furthermore, as component C, the coating materials according to the invention contain plasticizers, preferably lipophilic plasticizers. Especially suitable plasticizers are tributyl citrate, acetyltributyl citrate, triacetin, triethyl citrate, diethyl sebacate and dibutyl sebacate.

Components D

The coating materials used according to the invention for pharmaceutical dosage forms can contain, as components D, additionally at least one other pharmaceutically acceptable excipient. The excipients known to be usable in the area of pharmacy, food technology and related areas, in particular those listed in relevant pharmacopeias (e.g. Ph. Eur., USP, JP) and other excipients whose properties are not opposed to physiological use, are pharmaceutically acceptable.

Suitable excipients can be: flavorings, taste improvers, sweetening agents (sugars, sugar alcohols, sweeteners e.g. aspartame, saccharin-Na, sodium cyclamate), glidants, wetting agents, separating agents, antisticking agents, stabilizers, pore-forming agents, neutralizing agents, gloss agents, dyes, pigments, disinfectants or preservatives, thickening agents, etc. Such substances are described for example in Fiedler, H. P. Lexikon der Hilfsstoffe für Pharmazie, Kosmetik and angrenzende Gebiete (Lexicon of excipients for pharmacy, cosmetics and related areas), 4th edition, Aulendorf: ECV-Editio-Cantor-Verlag, 1996.

Usual amounts of the excipients are in a range in each case from 0 to 70 wt. %, preferably 0-60 wt. %, in particular 1-50 wt. %, relative to the total weight of solid matter in the coating material.

The coating material can be produced e.g. by intimate mixing of a polymer dispersion according to the invention, or a polymer obtainable therefrom by a drying process, with at least one excipient.

The coating material according to the invention can be used e.g. in powder form, as melt or in aqueous emulsion by granulation, pouring, spreading or by spray application. Application as polymer dispersion, especially as primary dispersion, is preferred. The coating materials according to the invention can additionally contain at least one other polymer component. It is then possible to use mixtures of at least two dispersions, at least one dispersion and at least one solution, at least one dispersion and at least one powder, at least two powders, etc.

The coating materials according to the invention are suitable for dosage forms basically of any pharmaceutical active compounds, which can preferably be administered in isolated or protected form, such as antidepressants, beta blockers, antidiabetic agents, analgesics, antiphlogistics, antirheumatics, antihypotensives, antihypertensives, psychoactive drugs, tranquilizers, antiemetics, muscle relaxants, glucocorticoids, agents for the treatment of ulcerative colitis or Crohn's disease, antiallergic agents, antibiotics, antiepileptics, anticoagulants, antimycotics, antitussives, arteriosclerotic agents, diuretics, enzymes, enzyme inhibitors, gout agents, hormones and inhibitors thereof, cardiac glycosides, immunotherapeutic agents and cytokines, laxatives, antilipemic agents, gastrointestinal therapeutic agents, antimigraine agents, preparations of minerals, otologic agents, antiparkinsonian agents, thyroid therapeutic agents, spasmolytics, antiplatelet agents, vitamins, cytostatics and metastasis inhibitors, phytopharmaceuticals, chemotherapy agents, nutraceuticals, vitamins, carotinoids and amino acids.

Examples of suitable active compounds are: acarbose, non-steroidal antirheumatics, cardiac glycosides, acetylsalicylic acid, virustatic agents, aclarubicin, aciclovir, cisplatin, actinomycin, α- and β-sympathomimetics, allopurinol, alosetron, alprostadil, prostaglandins, amantadine, ambroxol, amlodipine, methotrexate, 5-aminosalicylic acid, amitriptyline, amlodipine, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cephalosporins, celetoxib, cetirizine, chenodeoxycholic acid, ursodeoxycholic acid, theophylline and theophylline derivatives, trypsin, cimetidine, clarithromycin, clavulanic acid, clindamycin, clobutinol, clonidine, cotrimoxazole, codeine, caffeine, vitamin D and derivatives of vitamin D, colestyramine, cromoglycic acid, coumarin and coumarin derivatives, cysteine, cytarabine, cyclophosphamide, cyclosporin, cyproterone, cytarabine, dapiprazole, desogestrel, desonide, dihydralazine, diltiazem, ergot alkaloids, dimenhydrinate, dimethylsulfoxide, dimeticone, dipyridamole, domperidone and domperidone derivatives, donepzil, dopamine, doxazosin, doxorubicin, doxylamine, dapiprazole, benzodiazepine, diclofenac, glycoside antibiotics, desipramine, econazole, ACE inhibitors, enalapril, ephedrine, epinephrin, epoetin and epoetin derivatives, morphinanes, calcium antagonists, irinotecan, modafinil, orlistat, peptide antibiotics, phenytoin, riluzole, risedronate, sildenafil, topiramate, macrolide antibiotics, esomeprazole, estrogen and estrogen derivatives, gestagen and gestagen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, flunarizine, fluorouracil, fluoxetine, flurbiprofen, ibuprofen, flutamide, fluvastatin, follitropin, formoterol, fosfomycin, furosemide, fusidic acid, galantamine, gallopamil, ganciclovir, gemfibrozil, gentamicin, ginkgo, St. John's-wort, glibenclamide, urea derivatives as oral antidiabetics, glucagon, glucosamine and glucosamine derivatives, glutathione, glycerol and glycerol derivatives, hypothalamus hormones, goserelin, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, iphosphamide, imipramine, indometacin, indoramin, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives; evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, penciclovir, oral penicillin, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, rosiglitazone, roxatidine, roxithromycin, ruscogenin, rutoside and rutoside derivatives, sabadilla, salbutamol, salmeterol, scopolamine, selegiline, sertaconazole, sertindole, sertraline, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiame, sumatriptan, suxamethonium chloride, tacrine, tacrolimus, taliolol, tamoxifen, taurolidine, tazarotene, tegaserod, temazepam, teniposide, tenoxicam, terazosin, terbinafine, terbutaline, terfenadine, terlipressin, tertatolol, tetracyclines, tetryzoline, theobromine, theophylline, butizine, thiamazole, phenothiazines, thiotepa, tiagabine, tiapride, propionic acid derivatives, ticlopidine, timolol, tinidazole, tioconazole, thioguanine, thioxolone, tiopramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpine, troxerutin, tulobuterol, tyramine, tyrothricin, urapidil, ursodeoxycholic acid, chenodeoxycholic acid, valaciclovir, valdecoxib, valproic acid, vancomycin, vecuronium chloride, venlafaxine, verapamil, vidarabine, vigabatrin, viloxazine, vinblastine, vincamine, vincristine, vindesine, vinorelbine, vinpocetine, viquidil, warfarin, xantinol nicotinate, xipamide, zafirlukast, zalcitabine, zanamivir, zidovudine, zolmitriptan, zolpidem, zopiclone, zotepine and the like.

The active compounds can if desired also be used in the form of their pharmaceutically acceptable salts or derivatives, and in the case of chiral active compounds, both optically active isomers and racemates or diastereoisomeric mixtures can be used. If desired, the compositions according to the invention can also contain two or more pharmaceutical active compounds.

According to the invention, the coating materials can be used for coating extrudates, minitablets, capsules, soft capsules, granules, pellets, micropellets, microcapsules, nanocapsules or crystals.

For production of dosage forms, the coated granules, pellets, micropellets, microcapsules, crystals can be mixed with suitable excipients and compacted to form tablets, which disintegrate in the aqueous environment of the oral cavity and release the coated fine formed product. Of particular importance are the so-called oral dispersibles, i.e. tablets that disintegrate in the mouth within a short time and release the taste-masked small formed product.

Furthermore, the coating materials can also be used advantageously for coating tablets.

Classes of active compounds and substances that can often produce an unpleasant bitter taste and can be formulated advantageously according to the invention, are for example:

analgesics and antirheumatics, such as paracetamol, diclofenac, aceclofenac, ibuprofen, ketoprofen, flurbiprofen, acetylsalicylic acid, levacetylmethadol and oxycodone;

psychoactive drugs, such as promethazines, donepezil, modafinil, nefazodone, reboxetine, sertindole and sertraline;

antibiotics, such as erythromycin, roxithromycin, clarithromycin, grepafloxacin, ciprofloxacin, levofloxacin, sparfloxacin, trovafloxacin and nevirapine;

beta blockers, such as propranolol, metoprolol, bisoprolol and nebivolol;

antidiabetics, such as metformin, miglitol and repaglinide;

$H_1$ antihistamines, such as diphenhydramine, fexofenadine and mizolastine;

$H_2$ antihistamines, such as cimetidine, famotidine, roxatidine, nizatidine, ticlopidine, cetirizine and ranitidine;

vitamins such as thiamine nitrate and quinidine sulfate, amyloprilose HCl, pseudoephedrine HCl, sildenafil, topiramate, granisetron, rebamipide, quinine HCl, etc. Also various salts of these active compounds can be formulated correspondingly.

The excellent taste-masking results from the insolubility of the polymers according to the invention at pH above 6 and the rapid solubility at pH below 6. That is, in the saliva (pH: 7.2) correspondingly coated forms are stable for a very long time and there is no contact of the bitter medicinal product with the oral mucosae, but in the stomach at pH of 1-5 there is very rapid release of the active compound. Dissolution is then so rapid that there is no difference in the onset of action compared with an uncoated form. As a rule film coatings of a polymer according to the invention dissolve within 5 min in gastric juice, whereas in phosphate buffer pH 7.2 they are stable over 2 hours. Surprisingly, the film coatings also dissolve relatively quickly in media with pH values of 4.5, so that the dosage forms produced from them act quickly even in anacidic patients or patients being treated with antacids.

The coating materials according to the invention have good resistance to variations in release under temperature stress. In many cases there is also pronounced resistance to yellowing. Furthermore, there is also an advantageous effect on permeability to water vapor.

EXAMPLES

Abbreviations used:
BHT: butyl hydroxybenzene
BHA: butyl hydroxyanisole
NAC: N-acetylcysteine
ATBC: acetyltributyl citrate
TEC: triethyl citrate
MEHQ: hydroquinone monomethyl ether
d: days
Ludipress®: formulated product from lactose (90%), povidone (3.5%) and crospovidone (3.5%)
Avicel® PH 102: microcrystalline cellulose
Kollidon® VA 64: vinyl pyrrolidone-vinyl acetate (6:4) copolymer (copovidone)
Kollidon® CL: crosslinked polyvinylpyrrolidone (crospovidone)
All percentages relate to wt. %.
Cationic Polymers:
The production of the polymers is carried out as in example 1 of WO 2009/016258.
Polymer A: methyl methacrylate/diethylaminoethyl methacrylate, weight ratio 60:40,
Polymer B: methyl methacrylate/diethylaminoethyl methacrylate, weight ratio 55:45
Polymer C: methyl methacrylate/diethylaminoethyl methacrylate, weight ratio 53:47
The K values measured 0.1 by weight in NMP were 50+/−0.5

The polymers were used as 30 wt. % aqueous dispersions with a pH of 9+/−0.3. The average particle size of the primary dispersion was 110 nm.

Production of Polymer Films

The lipid-soluble antioxidants were stirred in the amounts stated in each case into the plasticizer component and were dissolved completely. This mixture was emulsified in water, producing an approx. 5% emulsion. This was added to aqueous polymer dispersion while stirring, optionally adjusted with water to a solids concentration of 20% and stirred for a further two hours.

In the case of water-soluble antioxidants, these were dissolved in the aqueous phase, before the plasticizer was incorporated by emulsifying.

The spray suspension was processed by means of a film sprayer (type FSG1, made by Heller) to an isolated film with a layer thickness of 200 μm. The processing temperature was selected so that during spraying the film had a temperature in the region of 33° C., final drying being carried out at 50° C.

Standard film (cationic polymer+15 wt. %, based on polymer, tributyl citrate)

Measurement of the Permeation of Water Vapor—General Method

The permeation of water vapor for selected films was determined according to DIN EN ISO 7783-2. Determination was carried out at a moisture gradient of 50/93% rel. humidity at 23° C.

Testing of the Films for Yellowing—General Method

The films were irradiated in a Suntest instrument (type Suntest COS plus, from the company Atlas) for 16 h with a luminous intensity of 765 W/m². Then the films were investigated by means of a colorimetric measuring instrument (type Datacolor 400, from the company Datacolor) for the so-called "b value", which is a measure of yellowing.

In the following, delta b corresponds to the change in the b value relative to the initial value.

Determination of the release from dosage forms was carried out with the equipment with a paddle stirrer described under Dissolution in the pharmacopeia of the USA (USP 32).

The dissolution time of films was also determined with the equipment with paddle stirrer described under Dissolution in the pharmacopeia of the USA (USP 32), the films with an average layer thickness of 200 μm being clamped in a slide frame (35×23 mm) and then immersed with a special device in a release instrument. The orientation of the slide frame was radial and the distance from the surface of the liquid was 3 cm.

The paddle stirrer rotated at 50 rpm, the volume of the medium 0.08 N-HCl was 900 ml and the temperature of the medium was 37° C.

The dissolution time is the time in which the film dissolves completely.

Example 1

Yellowing

| Additive | b value before irradiation | b value after 16 h UV | Delta b value |
|---|---|---|---|
| Polymer B without additive | 2.3 | 6.3 | 4.0 |
| Acetylcysteine 0.5% | 3.5 | 5.8 | 2.3 |
| Acetylcysteine 1% | 3.2 | 4.4 | 1.2 |
| Acetylcysteine 3% | 3.1 | 1.7 | −1.4 |
| Butyl hydroxytoluene 1% | 3.6 | 2.6 | −1.0 |
| Butyl hydroxytoluene 1% + Na-EDTA 1% | 3.2 | 1.8 | −1.4 |

-continued

| Additive | b value before irradiation | b value after 16 h UV | Delta b value |
|---|---|---|---|
| Butyl hydroxyanisole 2.5% | 3.3 | 4.0 | 0.7 |
| Sodium carbonate 10% | 3.3 | 3.2 | −0.1 |

Dissolution Time

| Additive | Dissolution time in 0.08N HCl Start value [min:s] | Dissolution time in 0.08N HCl 5 d/70° C. [min:s] |
|---|---|---|
| Without additive | 7:34 | >60 |
| Acetylcysteine 1% | 7:33 | 17:09 |
| Acetylcysteine 3% | 6:59 | 10:26 |
| Arginine 5% | 6:01 | 10:32 |
| Butyl hydroxyanisole 2.55% | 6:01 | 9:16 |
| Butyl hydroxytoluene 1% | 7:47 | 13:00 |
| Butyl hydroxytoluene 2.55% | 7:26 | 8:18 |
| Catechol 2.55% | 5:58 | 9:06 |
| Citric acid 0.5%/BHT 1% | 5:35 | 7:01 |
| Cysteamine 2.55% | 8:01 | 15:50 |
| Gallic acid 2.55% | 6:40 | 9:04 |
| Caffeic acid 2.55% | 7:46 | 12:09 |
| Lysine 5% | 5:05 | 16:36 |
| MEHQ 0.86% | 5:55 | 8:27 |
| Sodium carbonate 10% | 4:59 | 5:07 |
| Propyl gallate 0.86% | 6:02 | 10:42 |

Permeation of Water Vapor

| Additive | g/m² × 24 h/100 μm |
|---|---|
| Polymer B without additive | 71 |
| Butyl hydroxytoluene 1% | 61 |
| Butyl hydroxytoluene 2.5% | 57 |
| Acetylcysteine 0.5% | 67 |
| Tocopherol acetate 1% | 60 |

Example 2

Coated Caffeine Tablet 50 mg

Tablet Recipe:

| | |
|---|---|
| Ludipress | 239 mg |
| Avicel PH 101 | 40 mg |
| Caffeine, anhydrous fine powder | 50 mg |
| Magnesium stearate | 1 mg |
| Tablet weight | 330 mg |
| Method | Direct tableting |
| Tablet shape | Convex |
| Diameter | 9 mm |

Spray Recipe:

| | without BHT | with 2.5% BHT in the film |
|---|---|---|
| Polymer B (30% dispersion) | 37.78 | 33.33% |
| Tributyl citrate | 1.57 | 1.50% |
| Butyl hydroxytoluene | — | 0.5 |
| Talc | 6% | 6% |
| Titanium dioxide | 2% | 2% |
| Deionized water | 55.65% | 56.67% |
| Solids content | 20% | 20% |

Coating Conditions:

| | |
|---|---|
| Machine | Accela Cota 24/ horizontal drum coater |
| Inlet air temperature | 55° C. |
| Spraying pressure | 2 bar |
| Shaping air pressure | 1 bar |
| Spray nozzle | Schlick 930/1 mm |
| Air supply rate | 200 m³/h |
| Charge | 7 kg |
| Spraying rate | 30 g/min |
| Application rate | 4.5 mg/cm² |

Result:

Release in 0.08N Hydrochloric Acid

| Time, min | without BHT initial value % | with 2.5% BHT initial value % | without BHT 5 d/70° C. % | with 2.5% BHT 5 d/70° C. % |
|---|---|---|---|---|
| 5 | 65.2 | 57.8 | 2.9 | 9.1 |
| 10 | 98.1 | 95.8 | 7.2 | 42.5 |
| 15 | 103.6 | 104.3 | 33.2 | 75.3 |
| 20 | 103.8 | 103.1 | 63.0 | 85.9 |
| 30 | 103.0 | 100.0 | 95.4 | 103.5 |
| 45 | 102.8 | 102.0 | 102.1 | 102.8 |
| 60 | 102.0 | 101.0 | 103.2 | 101.3 |
| 90 | 101.0 | 103.0 | 101.9 | 105.0 |
| 120 | 101.3 | 102.1 | 102.6 | 102.1 |

Release in Phosphate Buffer pH 6.8

| Time, min | without BHA initial value % | with 2.5% BHA initial value % | without BHA 5 d 70° C. % | with 2.5% BHA 5 d 70° C. % |
|---|---|---|---|---|
| 5 | 0.1 | 0.3 | 0.2 | 0.2 |
| 10 | 0.2 | 0.2 | 0.3 | 0.5 |
| 15 | 0.3 | 0.4 | 0.1 | 0.5 |
| 20 | 0.9 | 0.7 | 0.4 | 0.3 |
| 30 | 1.0 | 0.9 | 0.5 | 0.9 |
| 45 | 1.9 | 1.4 | 0.8 | 1.3 |
| 60 | 2.5 | 2.6 | 1.6 | 1.5 |
| 90 | 4.3 | 4.1 | 2.5 | 2.1 |
| 120 | 6.3 | 6.0 | 5.7 | 5.4 |

Change in Yellowing

| Tablet | b value before irradiation | b value after 16 h UV irradiation | Delta b value |
|---|---|---|---|
| without BHT | 3.9 | 7.8 | 3.9 |
| with 2.5% BHT | 3.3 | 3.5 | 0.2 |

Example 3

Coated Quinine Sulfate Tablet 100 mg

Tablet Recipe:

| | |
|---|---|
| Quinine sulfate | 100 mg |
| Avicel PH 101 | 199 mg |
| Magnesium stearate | 1 mg |
| Tablet weight | 300 mg |
| Method | Direct tableting |
| Tablet shape | convex |
| Diameter | 9 mm |

Spray Recipe:

| | without arginine | with 5% arginine in the film |
|---|---|---|
| Polymer B (30% dispersion) | 33.33% | 30.43% |
| Tributyl citrate | 1.5% | 1.37% |
| Arginine | — | 1% |
| Talc | 6% | 6% |
| Titanium dioxide | 2% | 2% |
| Red iron oxide | 0.5% | 0.5% |
| Deionized water | 56.67% | 58.70% |
| Solids content | 20% | 20% |

Coating Conditions:

| | |
|---|---|
| Machine | Accela Cota 24/ horizontal drum coater |
| Inlet air temperature | 55° C. |
| Spraying pressure | 2 bar |
| Shaping air pressure | 1 bar |
| Spray nozzle | Schlick 930/1 mm |
| Air supply rate | 200 m³/h |
| Charge | 7 kg |
| Spraying rate | 30 g/min |
| Application rate | 4.5 mg/cm² |

Release in 0.08N Hydrochloric Acid

| Time, min | without arginine Initial value % | with 5% arginine Initial value % | without arginine 5 d/70° C. % | with 5% arginine 5 d/70° C. % |
|---|---|---|---|---|
| 5 | 55.3 | 66.3 | 3.9 | 13.1 |
| 10 | 88.3 | 94.9 | 9.2 | 44.5 |
| 15 | 99.6 | 101.3 | 36.2 | 82.3 |
| 20 | 102.1 | 102.1 | 73.0 | 95.9 |
| 30 | 103.3 | 103.0 | 95.0 | 101.5 |
| 45 | 102.1 | 102.9 | 102.9 | 102.1 |
| 60 | 102.1 | 101.6 | 101.2 | 100.3 |
| 90 | 100.9 | 103.1 | 103.9 | 104.9 |
| 120 | 101.1 | 103.6 | 102.4 | 102.7 |

Release in Phosphate Buffer pH 6.8

| Time, min | without arginine initial value % | with 5% arginine initial value % | without arginine 5 d/70° C. % | with 5% arginine 5 d/70° C. % |
|---|---|---|---|---|
| 5 | 0.1 | 0.3 | 0.2 | 0.2 |
| 10 | 0.3 | 0.6 | 0.3 | 0.5 |
| 15 | 0.4 | 0.5 | 0.1 | 0.5 |
| 20 | 0.8 | 0.9 | 0.4 | 0.8 |
| 30 | 1.3 | 1.9 | 0.5 | 0.9 |
| 45 | 0.9 | 2.5 | 0.4 | 1.3 |
| 60 | 1.1 | 3.3 | 0.6 | 1.5 |
| 90 | 1.3 | 4.2 | 0.5 | 2.1 |
| 120 | 1.6 | 6.3 | 0.7 | 2.4 |

Example 3

Coated Pseudoephedrine HCl Tablet 50 mg

Tablet Recipe:

| | |
|---|---|
| Pseudoephedrine HCl | 50 mg |
| Dicalcium phosphate | 95 mg |
| Kollidon 30 | 5 mg |
| PEG 6000 | 20 mg |
| Aerosil 200 | 2 mg |
| Tablet weight | 172 mg |
| Method | Moist granulation |
| Tablet shape | convex |
| Diameter | 7 mm |

Spray Recipe:

| | without BHA | with 2.5% BHA in the film |
|---|---|---|
| Polymer B (30% dispersion) | 36.23 | 34.78 |
| Triacetin | 1.63 | 1.57 |
| Butyl hydroxyanisole | — | 0.5% |
| Talc | 7% | 7% |
| Yellow iron oxide | 0.5% | 0.5% |
| Deionized water | 54.64% | 55.65% |
| Solids content | 20% | 20% |

Coating Conditions:

| | |
|---|---|
| Machine | Accela Cota 24/ horizontal drum coater |
| Inlet air temperature | 57° C. |
| Spraying pressure | 2 bar |
| Shaping air pressure | 1 bar |
| Spray nozzle | Schlick 930/1 mm |
| Air supply rate | 200 m³/h |
| Charge | 7 kg |
| Spraying rate | 35 g/min |
| Application rate | 6.0 mg/cm² |

Release in 0.08N Hydrochloric Acid

| Time, min | without BHA Initial value % | with 2.5% BHA Initial value % | without BHA 5 d/70° C. % | with 2.5% BHA 5 d/70° C. % |
|---|---|---|---|---|
| 5 | 35.3 | 37.3 | 3.1 | 11.3 |
| 10 | 68.9 | 71.9 | 6.2 | 41.3 |

-continued

| Time, min | without BHA Initial value % | with 2.5% BHA Initial value % | without BHA 5 d/70° C. % | with 2.5% BHA 5 d/70° C. % |
|---|---|---|---|---|
| 15 | 79.3 | 80.9 | 32.9 | 70.0 |
| 20 | 100.1 | 102.6 | 63.6 | 90.8 |
| 30 | 103.9 | 103.1 | 84.3 | 100.5 |
| 45 | 101.1 | 101.9 | 99.9 | 101.1 |
| 60 | 102.2 | 101.3 | 101.3 | 101.3 |
| 90 | 101.9 | 101.1 | 103.1 | 102.6 |
| 120 | 103.1 | 101.6 | 101.3 | 102.2 |

Release in Phosphate Buffer pH 6.8

| Time, min | without BHA Initial value % | with 2.5% BHA Initial value % | without BHA 5 d/70° C. % | with 2.5% BHA 5 d/70° C. % |
|---|---|---|---|---|
| 5 | 0.1 | 0.3 | 0.2 | 0.2 |
| 10 | 0.2 | 0.2 | 0.3 | 0.5 |
| 15 | 0.3 | 0.4 | 0.1 | 0.5 |
| 20 | 0.9 | 0.7 | 0.4 | 0.3 |
| 30 | 1.0 | 0.9 | 0.5 | 0.9 |
| 45 | 1.9 | 1.4 | 0.8 | 1.3 |
| 60 | 2.5 | 2.6 | 1.6 | 1.5 |
| 90 | 4.3 | 4.1 | 2.5 | 2.1 |
| 120 | 6.3 | 6.0 | 5.7 | 5.4 |

Example 4

Coated Loperamide Hydrochloride Tablet 2 mg

Tablet Recipe:

| | |
|---|---|
| Loperamide HCl | 2 mg |
| Avicel PH 101 | 195 mg |
| Aerosil 200 | 2 mg |
| Magnesium stearate | 1 mg |
| Tablet weight | 200 mg |
| Method | Direct tableting |
| Tablet shape | convex |
| Diameter | 8 mm |

Spray Recipe:

| | without acetylcysteine | with 3% acetylcysteine in the film |
|---|---|---|
| Polymer B (30% dispersion) | 34.78% | 33.04% |
| Triethyl citrate | 1.57% | 1.49% |
| Acetylcysteine | — | 0.6% |
| Talc | 6% | 6% |
| Titanium dioxide | 2% | 2% |
| Deionized water | 55.65% | 56.87% |
| Solids content | 20% | 20% |

Coating Conditions:

| Machine | Accela Cota 24/ horizontal drum coater |
|---|---|
| Inlet air temperature | 54° C. |
| Spraying pressure | 2 bar |
| Shaping air pressure | 1 bar |
| Spray nozzle | Schlick 930/1 mm |
| Air supply rate | 200 m³/h |
| Charge | 7 kg |
| Spraying rate | 30 g/min |
| Application rate | 3.0 mg/cm² |

Release in 0.08N Hydrochloric Acid

| Time, min | without ACC initial value % | with 3% ACC initial value % | without ACC 5 d/70° C. % | with 3% ACC 5 d/70° C. % |
|---|---|---|---|---|
| 5 | 15.3 | 17.3 | 3.0 | 9.3 |
| 10 | 26.9 | 28.9 | 4.2 | 23.9 |
| 15 | 47.3 | 51.3 | 19.9 | 48.9 |
| 20 | 75.2 | 78.9 | 49.1 | 78.6 |
| 30 | 98.9 | 101.1 | 64.3 | 94.5 |
| 45 | 101.1 | 102.9 | 89.5 | 100.1 |
| 60 | 102.4 | 100.6 | 100.3 | 101.3 |
| 90 | 101.0 | 101.2 | 101.1 | 101.1 |
| 120 | 102.1 | 101.7 | 103.3 | 103.6 |

Release in Phosphate Buffer pH 6.8

| Time, min | without ACC Initial value % | with 3% ACC Initial value % | without ACC 5 d 70° C. % | with 3% ACC 5 d 70° C. % |
|---|---|---|---|---|
| 5 | 0.1 | 0.3 | 0.2 | 0.2 |
| 10 | 0.4 | 0.2 | 0.3 | 0.4 |
| 15 | 0.3 | 0.5 | 0.1 | 0.5 |
| 20 | 0.8 | 0.7 | 0.4 | 0.3 |
| 30 | 1.1 | 0.9 | 0.5 | 0.9 |
| 45 | 1.2 | 1.4 | 0.8 | 1.3 |
| 60 | 2.5 | 2.8 | 1.8 | 1.5 |
| 90 | 3.3 | 4.9 | 2.6 | 3.1 |
| 120 | 4.4 | 9.5 | 3.7 | 8.5 |

Change in Yellowing

| Tablet | b value before irradiation | b value after 16 h UV irradiation | Delta b value |
|---|---|---|---|
| without ACC | 3.8 | 7.9 | 4.1 |
| with 3% ACC | 3.7 | 4.5 | 0.8 |

Example 5

Coated Paracetamol Tablet 500 mg

Tablet Recipe:

| | |
|---|---|
| Paracetamol | 500 mg |
| Avicel PH 102 | 137 mg |
| Kollidon VA 64 | 35 mg |
| Kollidon CL | 21 mg |
| Aerosil 200 | 4 mg |
| Magnesium stearate | 3 mg |
| Tablet weight | 700 mg |
| Method | Direct tableting |
| Tablet shape | convex |
| Diameter | 12 mm |

Spray Recipe:

|  | without sodium carbonate | with 10% sodium carbonate in the film |
|---|---|---|
| Polymer A (30% dispersion) | 40.58% | 34.78% |
| Triethyl citrate | 1.82% | 1.57 |
| Sodium carbonate | — | 2% |
| Talc | 3% | 3% |
| Titanium dioxide | 2% | 2% |
| Indigotin varnish | 1% | 1% |
| Deionized water | | |
| Solids content | 20% | 20% |

Coating Conditions:

| Machine | Accela Cota 24/ horizontal drum coater |
|---|---|
| Inlet air temperature | 56° C. |
| Spraying pressure | 2 bar |
| Shaping air pressure | 1 bar |
| Spray nozzle | Schlick 930/1 mm |
| Air supply rate | 200 m³/h |
| Charge | 7 kg |
| Spraying rate | 32 g/min |
| Application rate | 4.5 mg/cm² |

Release in 0.08N hydrochloric acid

| Time, min | without sodium carbonate Initial value % | with 10% sodium carbonate Initial value % | without sodium carbonate 5 d/70° C. % | with 10% sodium carbonate 5 d/70° C. % |
|---|---|---|---|---|
| 5 | 35.7 | 51.3 | 1.5 | 35.3 |
| 10 | 61.9 | 77.8 | 5.4 | 65.6 |
| 15 | 73.7 | 89.3 | 24.7 | 80.9 |
| 20 | 81.2 | 98.2 | 39.1 | 89.1 |
| 30 | 97.8 | 101.1 | 63.7 | 99.3 |
| 45 | 101.4 | 101.9 | 81.2 | 100.0 |
| 60 | 101.4 | 102.6 | 96.3 | 101.2 |
| 90 | 101.6 | 101.8 | 100.1 | 102.1 |
| 120 | 101.1 | 101.5 | 103.2 | 102.6 |

Example 6

Coated Caffeine Pellets

Pellet Recipe:

| Caffeine, anhydrous fine powder | 20% |
|---|---|
| Avicel PH 101 | 40% |
| Granulac 230 | 40% |
| Method | Extrusion, spheronization |
| Pellet diameter | 0.7-1.4 mm |

Spray Recipe:

|  | without BHT | with 2.5% BHT in the film |
|---|---|---|
| Polymer B (30% dispersion) | 39.42% | 37.97% |
| Tributyl citrate | 1.77% | 1.71% |
| Butyl hydroxytoluene | — | 0.5% |
| Talc | 6% | 6% |
| Titanium dioxide | 2% | 2% |
| Red iron oxide | 0.4% | 0.4% |
| Deionized water | 50.41% | 51.42% |
| Solids content | 20% | 20% |

Coating Conditions:

| Machine | Aeromatic Strea/ Wurster insert |
|---|---|
| Inlet air temperature | 56° C. |
| Spraying pressure | 1.3 bar |
| Nozzle diameter | 0.8 mm |
| Air supply rate | 85-100 m³ |
| Charge | 0.5 kg |
| Spraying rate | 8 g/min |
| Application rate | 4.5 mg/cm² |

Release in 0.08N Hydrochloric Acid

| Time, min | without BHT initial value % | with 2.5% BHT initial value % | without BHT 5 d/70° C. % | with 2.5% BHT 5 d/70° C. % |
|---|---|---|---|---|
| 5 | 10.1 | 14.8 | 4.5 | 13.1 |
| 10 | 34.8 | 33.9 | 19.5 | 30.8 |
| 15 | 59.9 | 57.1 | 41.7 | 52.8 |
| 20 | 76.8 | 73.1 | 55.8 | 71.9 |
| 30 | 88.9 | 85.9 | 78.9 | 87.5 |
| 45 | 97.6 | 95.1 | 92.1 | 95.2 |
| 60 | 98.7 | 98.1 | 95.3 | 99.8 |
| 90 | 101.3 | 100.3 | 101.1 | 101.4 |
| 120 | 102.1 | 101.5 | 100.7 | 103.1 |

Release in Phosphate Buffer pH 6.8

| Time, min | without BHT initial value % | with 2.5% BHT initial value % | without BHT 5 d/70° C. % | with 2.5% BHT 5 d/70° C. % |
|---|---|---|---|---|
| 5 | 0.8 | 0.6 | 0.7 | 0.3 |
| 10 | 0.6 | 1.8 | 0.7 | 0.5 |
| 15 | 0.6 | 1.7 | 0.5 | 0.5 |
| 20 | 0.6 | 1.8 | 0.9 | 0.5 |
| 30 | 0.6 | 1.9 | 0.7 | 0.5 |
| 45 | 1.0 | 1.5 | 0.4 | 0.6 |
| 60 | 1.1 | 1.5 | 0.7 | 0.8 |
| 90 | 0.9 | 1.6 | 0.9 | 0.9 |
| 120 | 0.6 | 1.7 | 1.1 | 1.1 |

Example 7

Coated Propranolol Pellets

Pellet Recipe:

| Propranolol HCl | 20% |
|---|---|
| Avicel PH 101 | 40% |
| Granulac 230 | 40% |
| Method | Extrusion, spheronization |
| Pellet diameter | 0.7-1.4 mm |

Spray Recipe:

|  | without BHT | with 1.7% BHT in the film |
|---|---|---|
| Polymer C (30% dispersion) | 59.1% | 59.1% |
| Tributyl citrate | 2.1% | 2.1% |
| Butyl hydroxytoluene | — | 0.5% |
| Talc | 6.6% | 6.1% |
| Titanium dioxide | 3% | 3% |
| Yellow iron oxide | 0.6% | 0.6% |
| Deionized water | 28.6% | 28.6% |
| Solids content | 30% | 30% |

Coating Conditions:

| Machine | Aeromatic Strea/ Wurster insert |
|---|---|
| Inlet air temperature | 62° C. |
| Spraying pressure | 1.3 bar |
| Nozzle diameter | 0.8 mm |
| Air supply rate | 85-100 m$^3$ |
| Charge | 0.5 kg |
| Spraying rate | 7 g/min |
| Application rate | 5.0 mg/cm$^2$ |

Release in 0.08N Hydrochloric Acid

| Time, min | without BHT initial value % | with 1.7% BHT initial value % | without BHT 5 d/70° C. % | with 1.7% BHT 5 d/70° C. % |
|---|---|---|---|---|
| 5 | 9.0 | 10.5 | 3.5 | 11.1 |
| 10 | 30.1 | 30.9 | 18.7 | 30.8 |
| 15 | 57.9 | 55.5 | 39.5 | 54.8 |
| 20 | 73.3 | 72.1 | 51.8 | 71.7 |
| 30 | 84.2 | 83.7 | 74.5 | 83.1 |
| 45 | 93.4 | 94.1 | 90.0 | 95.8 |
| 60 | 97.6 | 98.2 | 94.3 | 98.9 |
| 90 | 100.2 | 100.3 | 100.1 | 100.4 |
| 120 | 100.9 | 101.1 | 100.3 | 100.2 |

Release in Phosphate Buffer pH 6.8

| Time, min | without BHT initial value % | with 1.7% BHT initial value % | without BHT 5 d/70° C. % | with 1.7% BHT 5 d/70° C. % |
|---|---|---|---|---|
| 5 | 0.5 | 0.3 | 0.3 | 0.3 |
| 10 | 0.6 | 0.5 | 0.4 | 0.4 |
| 15 | 0.7 | 0.5 | 0.4 | 0.5 |
| 20 | 0.8 | 0.7 | 0.5 | 0.6 |
| 30 | 0.8 | 0.8 | 0.6 | 0.7 |
| 45 | 1.1 | 1.0 | 0.7 | 0.8 |
| 60 | 1.2 | 1.1 | 0.8 | 0.9 |
| 90 | 1.5 | 1.3 | 1.0 | 1.0 |
| 120 | 1.8 | 1.5 | 1.3 | 1.4 |

Example 8

Coated Paracetamol Crystals 0.2-0.5 mm

Spray Recipe:

|  | without BHT | with 3.3% BHT in the film |
|---|---|---|
| Polymer A (30% dispersion) | 26.7% | 26.7% |
| Acetyltributyl citrate | 1.3% | 1.3% |
| Butyl hydroxytoluene | — | 0.5% |
| Kaolin | 4.9% | 4.4% |
| Aspartame | 0.5% | 0.5% |
| Yellow iron oxide | 0.3% | 0.3% |
| Deionized water | 66.3% | 66.3% |
| Solids content | 15% | 15% |

Coating Conditions:

| Machine | Glatt GPC G1/ Wurster insert |
|---|---|
| Inlet air temperature | 63° C. |
| Spraying pressure | 1.4 bar |
| Nozzle diameter | 0.8 mm |
| Air supply rate | 100 150 m$^3$ |
| Charge | 1.2 kg |
| Spraying rate | 9 g/min |
| Application rate | 20 wt. % |

Release in 0.08N Hydrochloric Acid

| Time, min | without BHT initial value % | with 3.3% BHT initial value % | without BHT 5 d/70° C. % | with 3.3% BHT 5 d/70° C. % |
|---|---|---|---|---|
| 30 | 99.0 | 97.6 | 50.5 | 96.4 |
| 60 | 99.8 | 100.5 | 91.3 | 100.1 |

Release in Phosphate Buffer pH 6.8

| Time, min | without BHT initial value % | with 3.3% BHT initial value % | without BHT 5 d/70° C. % | with 3.3% BHT 5 d/70° C. % |
|---|---|---|---|---|
| 30 | 1.5 | 1.3 | 1.3 | 1.3 |
| 60 | 2.7 | 2.5 | 2.3 | 2.4 |

Examples 9-22

The film coatings described below were applied on the tablet cores from example 2 by the method described there.

| Example | Polymer | Plasticizer in the film (%) | Antioxidant in the film (%) | Other excipients in the film (%) | Solids concentration in the spray suspension (%) |
|---|---|---|---|---|---|
| 9 | A | TBC, 10% | BHT, 0.5% | Kaolin, 40% | 10 |
| 10 | B | Triacetin, 10% | BHA, 5.0% | — | 20 |
| 11 | B | ATBC, 7% | NAC, 1.0% | Talc, 60% | 30 |
| 12 | C | TBC, 11% | Arginine, 12% | Talc, 20% | 20 |
| 13 | C | TBC, | Spermidine, 1.0% | — | 8 |
| 14 | B | TEC, 20% | NAC, 0.5% | — | 5 |
| 15 | A | Triacetin, 10% Polyethylene glycol 10% | BHT, 2.5% | Saccharin-Na, 0.5% | 15 |
| 16 | C | TBC, 10% | Sodium carbonate, 20% | Titanium dioxide, 15% | 40 |
| 17 | A | ATBC, 8% TEC, 2% | Disodium hydrogen phosphate, 5% | Talc, 30% | 20 |
| 18 | A | TBC, 10% | BHT, 1% NAC, 1% | Talc, 10%, Titanium dioxide, 20% | 20 |
| 19 | B | TBC, 12% | Cysteamine, 2.5% | Talc, 20%, Sunset Yellow, 0.5% | 25 |
| 20 | B | TBC, 11 | BHT, 0.5%, EDTA 0.5% | Titanium dioxide, 30% | 15 |
| 21 | C | TBC, 10% | Propyl gallate, 1.5% | Talc, 35% | 20 |
| 22 | C | TEC, 10% | Lysine, 7.5% | Talc, 30% | 20 |

All recipes 9-22 showed a definite stabilization of release after storage as in example 2.

The invention claimed is:

1. A coating material containing a mixture of
i) a polymer obtained by radical polymerization from
  a) N,N-diethylaminoethyl methacrylate, and
  b) at least one radically polymerizable compound, selected from esters of α,β-ethylenically unsaturated mono- and dicarboxylic acids with $C_1$-$C_8$ alkanols, as component A,
ii) one or more antioxidants comprising N-acetylcysteine, arginine, lysine, butyl hydroxytoluene, butyl hydroxytoluene plus Na-EDTA, sodium carbonate, or combinations thereof, as component B,
iii) one or more plasticizers as component C, and
iv) other excipients as components D,
wherein the total amount of the mixture of components A-D is 100 wt. %.

2. The coating material of claim 1, containing a mixture of
i) 0.20-90 wt. % of component A
ii) 0.1-30 wt. % of component B
iii) 0.2-30 wt. % of component C
iv) 0-70 wt. % of components D.

3. The coating material of claim 1, containing a mixture of
i) 30-85 wt. % of component A
ii) 0.3-20 wt. % of component B
iii) 3-25 wt. % of component C
iv) 0-60 wt. % of components D.

4. The coating material of claim 1, containing a mixture of
i) 40-80 wt. % of component A
ii) 0.5-12 wt. % of component B
iii) 4-20 wt. % of component C
iv) 1-50 wt. % of components D.

5. The coating material of claim 1, wherein component A comprises a polymer of N,N-diethylaminoethyl methacrylate and methyl methacrylate.

6. The coating material of claim 1, containing, as component A, a polymer of:
43-47 wt. %, relative to the total weight of the monomers used for polymerization, of N,N-diethylaminoethyl methacrylate a), and
53-57 wt. %, relative to the total weight of the monomers used for polymerization, of methyl methacrylate.

7. The coating material of claim 1, wherein the coating material is in the form of an aqueous polymer dispersion.

8. The coating material of claim 7, wherein the aqueous polymer dispersion comprises 5-50 wt. % of the mixture of components A-D.

9. A method for the production of film coatings for pharmaceutical dosage forms, the method comprising using the coating materials of claim 1 for the production of film coatings for pharmaceutical dosage forms that disintegrate quickly in an acid environment.

10. A film coating for pharmaceutical dosage forms, containing a mixture of
i) a polymer obtained by radical polymerization from
  a) N,N-diethylaminoethyl methacrylate, and
  c) at least one radically polymerizable compound, selected from esters of α,β-ethylenically unsaturated mono- and dicarboxylic acids with $C_1$-$C_8$ alkanols, as component A,
ii) one or more antioxidants comprising N-acetylcysteine, arginine, lysine, butyl hydroxytoluene, butyl hydroxytoluene plus Na-EDTA, sodium carbonate, or combinations thereof, as component B,
iii) one or more plasticizers as component C, and
iv) other excipients as components D,
wherein the total amount of the mixture of components A-D is 100 wt. %.

11. The coating material of claim 1, wherein component C comprises one or more of tributyl citrate, acetyltributyl citrate, triacetin, triethyl citrate, diethyl sebacate and dibutyl sebacate.

12. The coating material of claim 4, wherein component A comprises a polymer of N,N-diethylaminoethyl methacrylate and methyl methacrylate.

13. The coating material of claim 4, wherein component A comprises a polymer of:
43-47 wt. %, relative to the total weight of the monomers used for polymerization, of N,N-diethylaminoethyl methacrylate a), and 53-57 wt. %, relative to the total weight of the monomers used for polymerization, of methyl methacrylate.

14. The method of claim 9, wherein component A comprises a polymer of N,N-diethylaminoethyl methacrylate and methyl methacrylate.

15. The method of claim 9, wherein component A comprises a polymer of:
- 43-47 wt. %, relative to the total weight of the monomers used for polymerization, of N,N-diethylaminoethyl methacrylate a), and
- 53-57 wt. %, relative to the total weight of the monomers used for polymerization, of methyl methacrylate.

16. The method of claim 9, wherein the coating material is in the form of an aqueous polymer dispersion.

17. The method of claim 16, wherein the aqueous polymer dispersion comprises 5-50 wt. % of the mixture of components A-D.

18. The method of claim 9, wherein component C comprises one or more of tributyl citrate, acetyltributyl citrate, triacetin, triethyl citrate, diethyl sebacate and dibutyl sebacate.

* * * * *